United States Patent
Okumura

Patent Number: 6,123,119
Date of Patent: Sep. 26, 2000

[54] METHOD OF TRANSFERRING A LIQUID SPECIMEN IN ONE CONTAINER ON A CENTRIFUGAL ROTOR INTO ANOTHER CONTAINER ON THE SAME ROTOR

[75] Inventor: Akira Okumura, Hyogo, Japan

[73] Assignee: Fumiko Uozumi, Kobe, Japan

[21] Appl. No.: 09/358,821

[22] Filed: Jul. 22, 1999

[30] Foreign Application Priority Data

Jul. 24, 1998 [JP] Japan ................................. 10-225258

[51] Int. Cl.$^7$ ................................................ B65B 1/04
[52] U.S. Cl. .......................... 141/34; 141/130; 210/787; 422/101
[58] Field of Search ........................... 422/101; 210/787, 210/788; 141/34, 2, 18, 69, 130

[56] References Cited

U.S. PATENT DOCUMENTS

| | | | |
|---|---|---|---|
| 4,154,793 | 5/1979 | Guigan | 141/34 |
| 4,708,710 | 11/1987 | Dunn, Jr. | 210/787 |
| 5,256,314 | 10/1993 | Driessen | 210/787 |

FOREIGN PATENT DOCUMENTS

| | | |
|---|---|---|
| 56-95354 | 8/1981 | Japan . |
| 56-144759 | 11/1981 | Japan . |
| 5-18658 | 3/1993 | Japan . |

*Primary Examiner*—Steven O. Douglas
*Attorney, Agent, or Firm*—Wenderoth, Lind & Ponack, L.L.P.

[57] ABSTRACT

A method for safely, reliably and continuously feeding a liquid specimen such as human blood in one container on a centrifugal rotor into another container on the same rotor without the need to touch the specimen as well as any part of the device while completely preventing contamination due to mixing of microorganisms. A liquid is injected into a pressurizing or a depressurizing container on a rotor from outside to pressurize or depressurize a first container on the rotor, thereby feeding under pressure a specimen in the first container into a second container on the same rotor, or sucking a specimen in the second container into the first container.

3 Claims, 8 Drawing Sheets

METHOD OF TRANSFERRING A LIQUID SPECIMEN IN ONE CONTAINER ON A CENTRIFUGAL ROTOR INTO ANOTHER CONTAINER ON THE SAME ROTOR

BACKGROUND OF THE INVENTION

The present invention belongs to separation, purification and analysis of liquid components, and relates to a method of transferring a liquid specimen in one container on a centrifugal rotor into another container on the same rotor, and more particularly to a method of injecting a liquid into a pressurizing or depressurizing container on a rotor from outside and pressurizing or depressurizing the interior of one container to feed a liquid specimen in the container under positive or negative pressure into another container.

In order to separate, purify or analyze a liquid specimen by use of a centrifugal rotor, it is necessary to stop the centrifugal rotor to manually aliquot the centrifuged components. But there are also known techniques that permit automatic separation, purification, and analysis of a liquid specimen without the need to stop the rotor, such as a method of aliquoting and discharging liquid components in a centrifugal rotor as disclosed in U.S. Pat. No. 1,124,173, a separating/mixing device and a separating/mixing/discharge device as disclosed in U.S. Pat. No. 1,135,888, and a separating/purifying/analyzing rotor as disclosed in Utility Model No. 2147917.

In automatic centrifugal separating arrangements, specimens or reagents are injected into specimen containers on a rotating rotor from outside through a distributor. In this case, it is difficult to completely prevent mixing of microorganisms into specimens. If the specimens are biological ones, mixing of microorganisms can create especially serious problems.

If a volatile liquid such as alcohol is injected from outside, it causes a problem. Noxious strong acids or alkalis are not desirable either.

An object of the present invention is to provide a method that makes it possible to separate, purify or analyze specimens, reagent solutions, or poisonous specimens/specimen solutions put in a container on a rotor in a safe manner while completely preventing contamination by microorganisms by transferring such specimens into another container on the same rotor while the rotor is rotating.

SUMMARY OF THE INVENTION

According to the present invention, there is provided a method of transferring a liquid specimen in one container on a centrifugal rotor into another container on the same rotor, the method comprising the step of injecting a liquid into a pressurizing container communicating with the one container while the rotor is rotating, to increase the volumetric ratio of liquid in the pressurizing container, thereby increasing the gas pressure in the pressurizing container and thus the gas pressure in the one container, thereby transferring the liquid specimen in the one container under pressure into the another container.

Figure 2A:
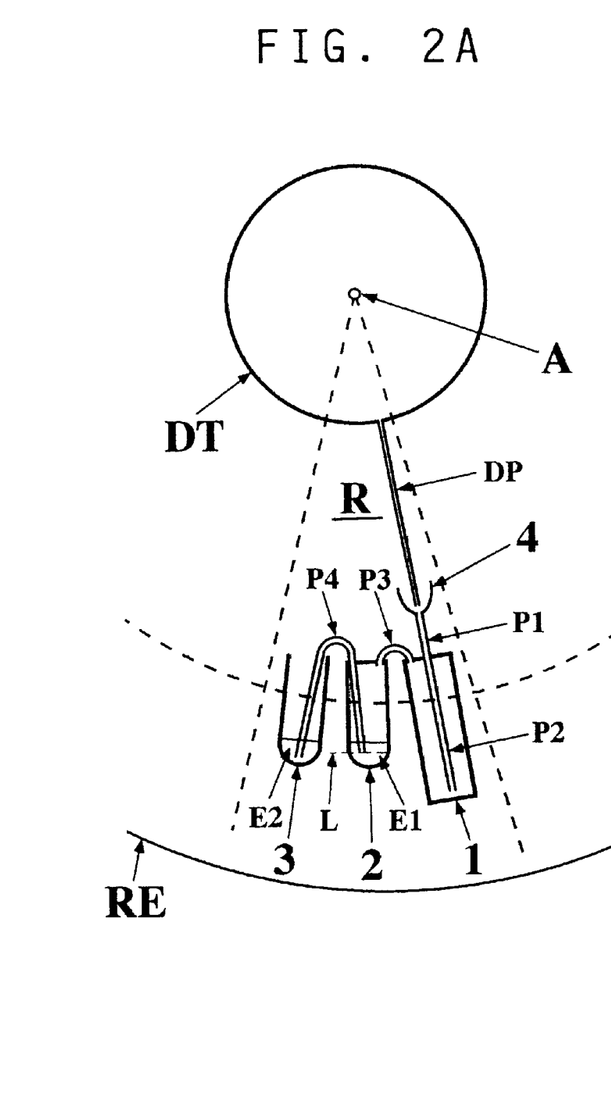
FIG. 2A is a schematic view showing an arrangement in which a pressurizing container is used as a pressurizer.

First, the basic function of the pressurizing container is briefly described. As shown in FIG. 2A, the top of the pressurizing container 1 is connected to the top of a specimen container 2 containing liquid E1 to be transferred (wherein the centrifugal force acts downward) through a pipe P3. A liquid container 3 containing a liquid E2 communicates with a liquid E1 in the container 2 through a pipe P4. When the pressure in the pressurizing container 1 rises, the pressure in the specimen container 2 rises, so that the liquid E1 in the container 2 is discharged under pressure into the container 3 and mixes with liquid E2.

According to the present invention, there is also provided a method of transferring a liquid specimen in one container on a centrifugal rotor into another container on the same rotor, the method comprising the step of injecting a liquid into a depressurizing container communicating with the another container while the rotor is rotating, discharging the liquid from the depressurizing container by centrifugal force to decrease the volumetric ratio of liquid in the depressurizing container to reduce the gas pressure in the depressurizing container and thus the gas pressure in the another container, thereby sucking the liquid specimen in the one container into the another container.

Figure 2B:
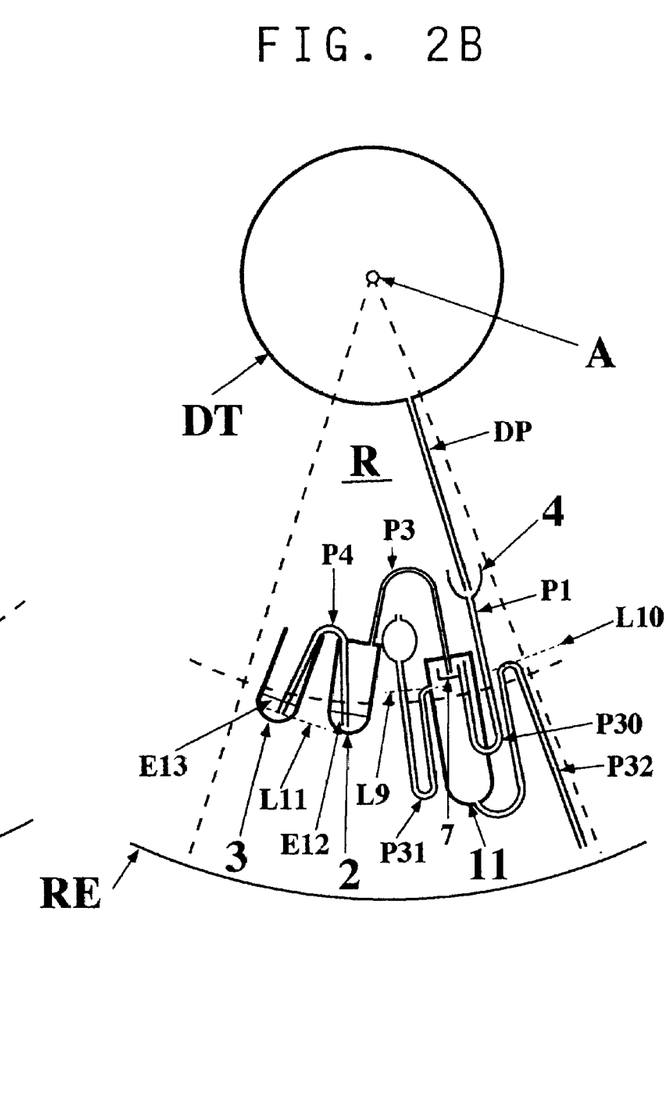
FIG. 2B is a similar view showing an arrangement in which a depressurizing container is used as a depressurizer.

The basic function of the depressurizing container is briefly described. As shown in FIG. 2B, the top of the depressurizing container 11 communicates with the top of a specimen container 2 containing specimen liquid E12 through a pipe P3. The container 2 containing liquid E12 communicates with liquid E13 in another specimen container 3. When the pressure in the depressurizing container 11 lowers by centrifugal force, the pressure in the specimen container 2 containing liquid E12 drops, so that liquid E13 is sucked from the container 3 into the specimen container 2 and mixes with liquid E12.

According to the present invention, there is provided a method of transferring a liquid specimen in one container on a centrifugal rotor into another container on the same rotor, the method comprising the step of injecting a liquid into a small depressurizing container communicating with the another container while the rotor is rotating, discharging the liquid quickly from the small depressurizing container through a discharge tube by centrifugal force to reduce the gas pressure in the small depressurizing container and thus the gas pressure in the another container, thereby sucking the liquid specimen in the one container into the another container.

Figure 7:
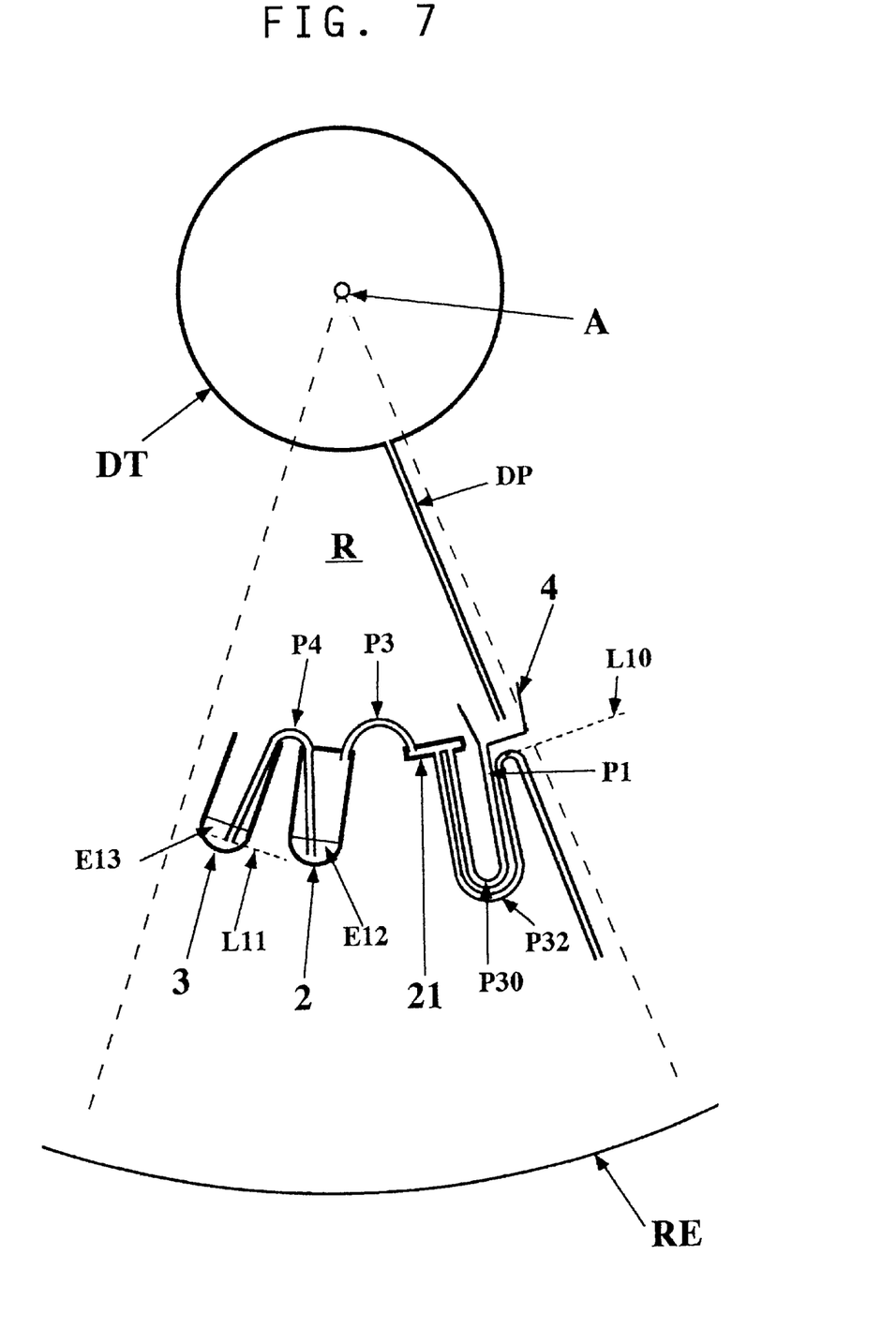
FIG. 7 is a view showing the fifth embodiment in which a small depressurizing container is used.

The basic function of the small depressurizing container is briefly described. As shown in FIG. 7, the small depressurizing container 21 communicates with a specimen container 2 containing specimen liquid E12 through a pipe P3. The specimen container 2 containing liquid E12 communicates with liquid E13 in another container 3. When the pressure in the specimen container 2 decreases, liquid E13 in the container 3 is sucked into the container 2, mixing with liquid E12.

Other features and objects of the present invention will become apparent from the following description made with reference to the accompanying drawings, in which:

DETAILED DESCRIPTION OF THE PREFERRED EMBODIMENT

Several embodiments of the present invention are now described with reference to the attached drawings.

Figure 1:
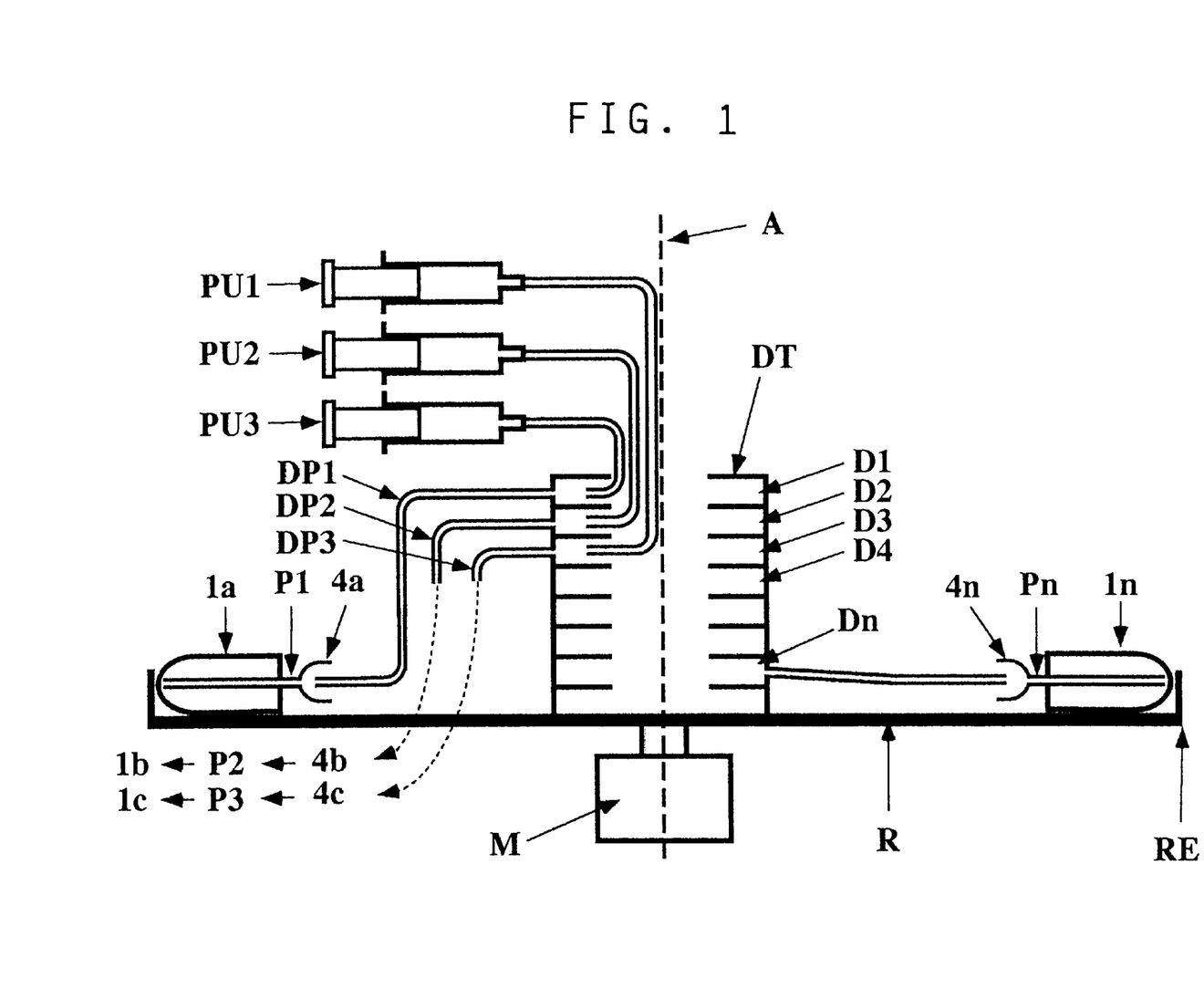
FIG. 1 is a schematic view of a device used to carry out the method embodying the present invention.

FIG. 1 schematically shows a device for injecting a liquid into a designated container on a rotor R without stopping the rotor. As shown, the device includes external injection pumps PU1–PUn (only PU1–PU3 shown), a distributor DT on the rotor, and pressurizing containers 1a–1n. The letter R designates the body of the centrifugal rotor rotated by a motor M (its rotary shaft is designated by A and its outer edge by RE). The cylindrical liquid distributor DT comprises a plurality of liquid injecting stages D1 to Dn arranged vertically at the central part of the rotor R. The liquid injection pumps PU1–PU3 have their tips communicating into the liquid injecting stages D1–D3, respectively.

The liquid injection stages D1–Dn communicate with the containers 1a–1n through injection pipes DP1–DPn, liquid reservoirs 4a–4n and end pipes P1–Pn.

When liquid is injected from the external injection pumps while the rotor R is rotating, the liquid flows into the liquid injection stages D1–Dn of the distributor DT which is rotating. Under the influence of centrifugal force of the rotor R, the liquid rotating together with the distributor DT flows in the centrifugal direction, that is, it flows through the pipe DP1, liquid reservoir 4a, end pipe P1 into the container 1a. Similarly, liquid injected by the injection pumps PU2 and PU3 flow into the containers 1b and 1c, respectively, in the same manner.

FIG. 2A shows a first arrangement of the method according to the present invention of transferring a liquid specimen in a container on the rotor into another container on the rotor by means of a pressurizing container. It shows the pressurizing container 1 as a pressurizer provided on the centrifugal rotor R, a specimen container 2 containing liquid E1, and another container 3 containing liquid E2, and pipes P3, P4 through which the containers communicate.

When a liquid is injected into the distributor DT on the rotor R which is rotating, the liquid flows through the injection pipe DP, liquid reservoir 4, end pipes P1, P2 into the pressurizing container 1, so that air in the container 1 is compressed and the pressure in the container 1 rises. When the pressure in the container rises, the container 1 functions as a pressurizer.

Air in the pressurizing container 1 is discharged under pressure through the pipe P3 into the container 2. In this embodiment, the amount of liquid injected into the pressurizing container 1, that is, the amount of air discharged under pressure from the pressurizing container 1 is set to be sufficiently large, so that the container 2 and the pressurizing container 1 communicate only through the pipe 3, and the containers 2 and 3 communicate only through the pipe P4. The liquid above the level L of liquid E1 remaining in the container 2, flows into the container 3 only through the pipe P4. Further, air is blown into the container 3, thus stirring the mix of liquids E1 and E2 (if the pipe P4 protrudes into the liquid mix).

Figure 3:
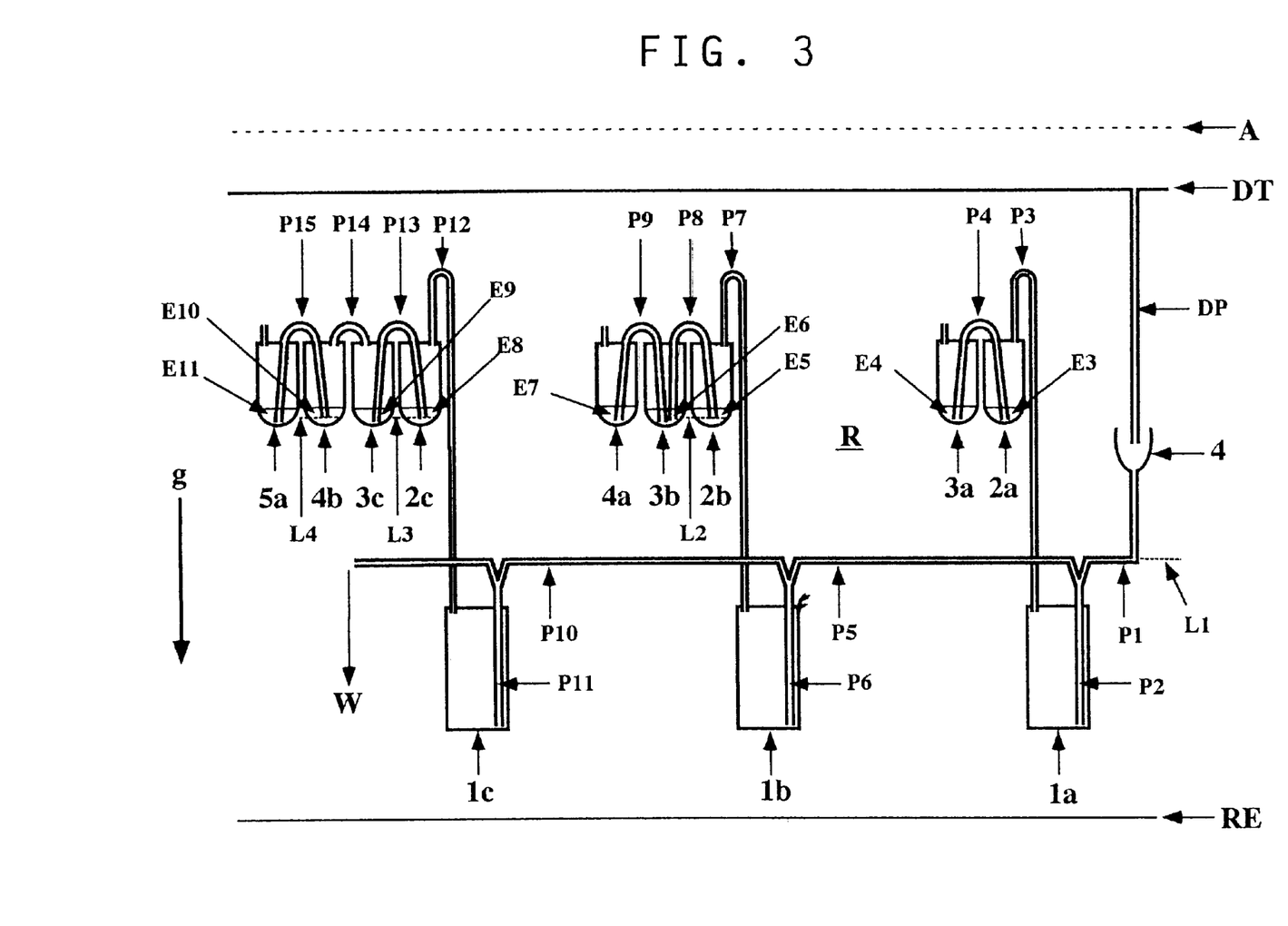
FIG. 3 is a view showing the first embodiment in which a pressurizing container is used.

FIG. 3 shows a first embodiment of the method according to the present invention of transferring a liquid specimen in one container on the rotor into another container on the rotor, by means of a pressurizing container. It shows a pressurizing container 1a as a first pressurizer, a pressurizing container 1b as a second pressurizer, and a pressurizing container 1c as a third pressurizer that are arranged in series on the centrifugal rotor R, and containers (2a, 3a), (2b, 3b, 4a), (2c, 3c, 4b, 5a) subordinate to the first, second and third pressurizing containers 1a, 1b, 1c, respectively. It shows how they communicate on the circumference of the rotor.

When liquid injected into the distributor DT flows through one of the stages of the distributor DT, injection pipe DP, liquid reservoir 4, pipe P1, pipe P2 into the pressurizing container 1a, air in the container 1a is compressed and the internal pressure rises.

Air in the pressurizing container 1a flows through the pipe P3 and is discharged under pressure into the container 2a. In this embodiment, the amount of fluid injected into the pressurizing container 1a is set to be large enough, so that liquid in the container 2a is entirely transferred into the container 3a because one end of the pipe P4 is at the bottom of the container 2a. Further, air is blown into and agitate the mixture of liquids E3 and E4 in the container 3a (if the pipe P4 protrudes into the liquid mix).

When the pressurizing container 1a is filled with liquid injected by the pump, liquid overflows through the pipes P5, P6 into the pressurizing container 1b. Air in the container 1b is thus compressed, and the internal pressure rises.

Air in the pressurizing container 1b flows through the pipe P7 and is discharged under pressure into the container 2b. In the same manner as above, the amount of liquid injected into the pressurizing container 1b is set to be large enough, so that any liquid above the level L2 of liquid E5 remaining in the container 2b flows through the pipe P8 into the container 3b and mixes with liquid E6. The liquid mix then flows through the pipe P9 into the container 4a and mix with liquid E7. Air is blown into and agitates the mixture of liquids E5, E6 and E7 in the container 4a (if the pipe P9 protrudes into the liquid mix).

When the pressurizing containers 1a and 1b are filled up with liquid injected by the pump, liquid overflows through the pipe P10, P11 into the pressurizing container 1c. Air in the container 1c is thus compressed, and the internal pressure rises.

Air in the pressurizing container 1c flows through the pipe P12 and is discharged under pressure into the container 2c. The amount of liquid injected into the container 1c is set to be large enough, so that any liquid above the level L3 of liquid E8 remaining in the container 2c flows through the pipe P13 into the container 3c and mixes with liquid E9. Any liquid above the level L4 of liquid E10 remaining in the container 4b flows through the pipe P15 into the container 5a and mixes with liquid E11. Air is blown into the containers 3c and 5a and agitates the liquid mixtures (if the pipes P13, P15 protrude into the respective liquid mixtures).

When the pressurizing containers 1a, 1b and 1c are filled up with injected liquid, liquid overflows and is discharged into a liquid reservoir W.

In FIG. 3, the first to third pressurizing containers 1a, 1b, 1c are arranged in series. But more than three pressurizers may be used. The number of containers subordinate to each pressurizer may also be increased. The containers may be interconnected in different ways.

Figure 4:
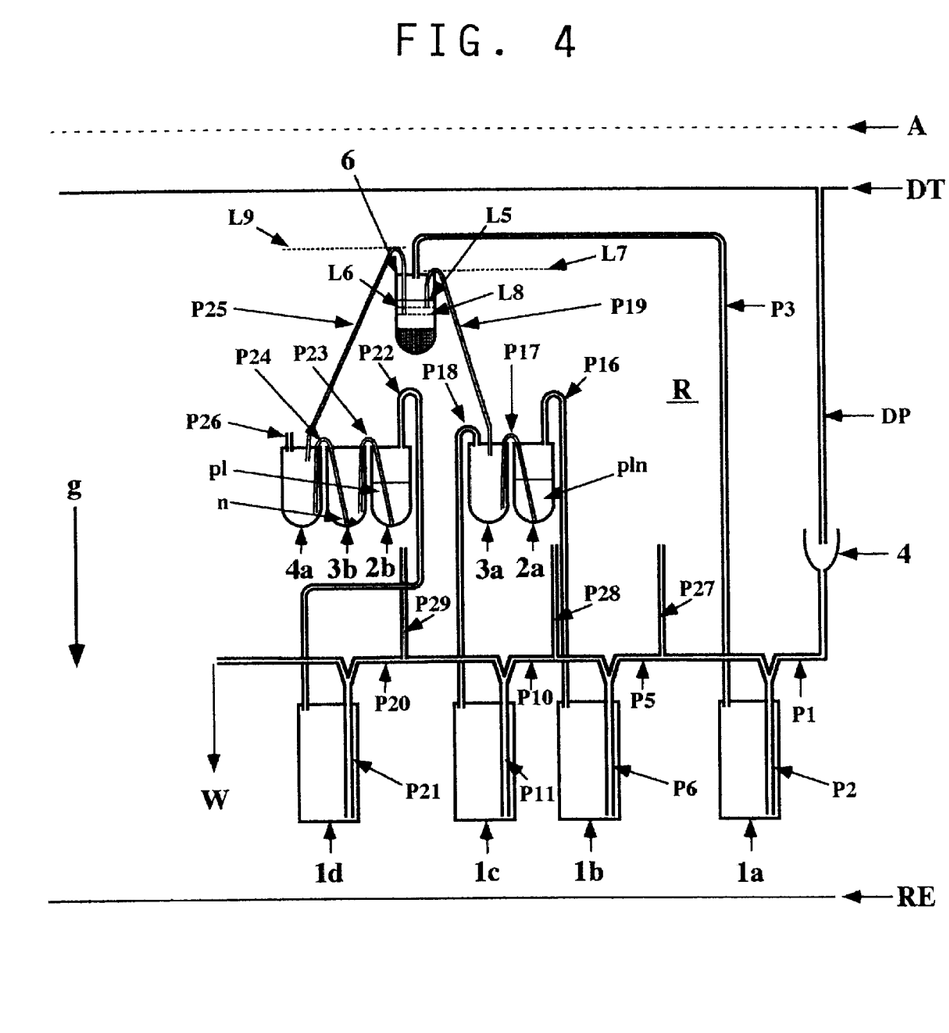
FIG. 4 is a view showing the second embodiment in which a pressurizing container is used.

FIG. 4 shows a second embodiment which is a variation of the arrangement of FIG. 2A in which a pressurizing container is used. It shows a pressurizing container 1a as a first pressurizer, a pressurizing container 1b as a second pressurizer, a pressurizing container 1c as a third pressurizer, and a fourth pressurizing container 1*d* as a fourth pressurizer that are arranged on the centrifugal rotor R, and containers (2*a*, 3*a*), (2*b*, 3*b*, 4*a*) and a plasma separating container 6. FIG. 4 shows how they communicate on the circumference of the rotor.

In the plasma separating container 6, 0.5 ml of human blood (extracted from one of the inventors of the present invention) to which was added a trace amount of heparin was put. In the container 2*a*, 0.9 ml pyrophosphate buffer p1n (pH8.3, 0.1M) containing reduced nicotinamide adenine dinucleotide ($10^{-3}$M) and pyruvate ($10^{-3}$M) as a reaction reagent was put. In the container 2*b*, 0.9 ml pyrophosphate buffer p1 (pH8.3, 0.1M) containing pyruvate ($10^{-3}$M) was put. In the container 3*b*, 0.66 mg of reduced nicotinamide adenine dinucleotide powder n was put.

The rotating centrifugal rotor R was observed visually while illuminating it with a lamp blinking synchronously with the rotation of the rotor.

After the blood has been centrifuged by rotating the rotor at 2000 rpm (about three minutes), liquid (water) was injected by a pump. When the water flows through one of the stages of the distributor DT, pipe DP, liquid reservoir 4, pipes P1, P2 into the pressurizing container 1*a*, air in the container 1*a* was compressed and the inner pressure rose.

Air in the pressurizing container 1*a* was pressurized and flowed through the pipe P3 into the container 6. The plasma between the level L5–L6 in the container (centrifuged supernatant of blood) flowed through the pipe P19 into the container 3*a*. (Since level L7 is lower than level L9, plasma flows out under pressure only through the pipe P19, and not through the pipe P25.) Further, gas fed under pressure into the container 3*a* was exhausted through the pipe P18, container 1*c*, pipe P11, pipe P10, pipe P28 (and partially through the pipe P10, pipe P5, pipe P27).

When the pressurizing container 1*a* has been filled up with liquid injected by the pump, liquid overflows through the pipe P5, pipe P6 into the pressurizing container 1*b*. Air in the container 1*b* was compressed and the inner pressure rose.

Air in the pressurizing container 1*b* was fed under pressure through the pipe P16 into the container 2*a*. Since the amount of liquid injected into the pressurizing container 1*b* was set to be large enough, liquid p1n in the container 2*a* [0.9 ml pyrophosphate buffer (pH8.3, 0.1M) containing reduced nicotinamide adenine dinucleotide (10 $^{-3}$M) and pyruvate ($10^{-3}$M)] flowed through the pipe P17 into the container 3*a* and mixed with the blood plasma in the container 3*a*. Further, air was blown into the liquid mix in the container 3*a* and agitated it (because the pipe P17 was open into the liquid). Air blown into the container 3*a* was exhausted through the pipe P18, pressurizing container 1*c*, pipe P11, pipe P10, pipe P28.

When the pressuring containers 1*a* and 1*b* had been filled up with liquid injected by the pump, liquid overflowed through the pipes P10, P11 into the pressurizing container 1*c*, so that the gas in the pressurizing container 1*c* was compressed and the internal pressure rose. At the same time, the exhaust passages of the pipes P11, P10, P28 were closed.

Gas in the pressuring container 1*c* was fed under pressure through the pipe P18, container 3*a*, pipe P19 into the container 6, so that plasma in the container 6 at the level between L6 and L8 was fed through the pipe P25 into the container 4*a*. Gas discharged under pressure into the container 4*a* was exhausted through P26.

When the pressurizing containers 1*a*, 1*b*, 1*c* had been filled up with liquid injected by the pump, liquid overflowed and was fed through the pipes P20, P21 into the container 1*d*, so that air in the pressurizing container 1*d* was compressed and the internal pressure rose.

Gas in the container 1*d* was discharged under pressure through the pipe P22 into the container 2*b*. Since the amount of liquid injected into the pressurizing container 1*d* was set to be large enough, liquid in the container 2*b* flowed through the pipe P23 into the container 3*b*, dissolving the reduced nicotinamide adenine dinucleotide powder n in the container 3*b*, and was further fed through the pipe P24 into the container 4*a*, mixing with blood plasma. Then, gas was blown into the liquid mix and agitated it (because the pipe P24 was open into the liquid).

When the pressuring chambers 1*a*, 1*b*, 1*c*, 1*d* were filled up with injected liquid, liquid overflowed and was discharged into the reservoir W.

How liquid moved and mixed and how gas was blown into liquid on the centrifugal rotor was visually observed using a device that permits visual observation under synchronously blinking illumination as described above, and the results of observation were duly recorded.

The supernatant of liquid in the plasma separating container 6 was fed 0.1 ml each into the containers 3*a* and 4*a* and mixed with reaction reagents. By the action of lactate dehydrogenase contained in blood (plasma), reduced nicotinamide adenine dinucleotide in the pyrophosphate buffer was oxidized. By measuring the oxidizing speed in terms of absorbance of light of 340 nm in wavelength with a photometer provided outside the rotor, it was possible to automatically determine the lactate dehydrogenase activity in the blood (plasma).

FIG. 2B shows a second arrangement of the method according to the present invention of transferring a liquid specimen in a container on the rotor into another container on the rotor, by means of a depressurizing container. It shows the depressurizing container 11 as a depressurizer provided on the centrifugal rotor R, a container 2 containing liquid E12, and another container 3 containing liquid E13, and shows how they communicate with each other.

When a liquid is injected into the distributor DT on the rotor R that is rotating, the liquid flows through the injection pipe DP, liquid reservoir 4, end pipe P1, U-pipe P30 into liquid reservoir tray 7 of the container 11. Liquid overflowing the tray increases the liquid level in the depressurizing container 11, so that gas in the depressurizing container 11 is exhausted through the exhaust pipe P31. When the liquid level further increases and exceeds the inlet level L9 of pipe P31, liquid now flows into the exhaust pipe P31, closing air communication through the exhaust pipe P31. When the level further increases and exceeds the siphon-activating level L10, liquid in the depressurizing container 11 is discharged through a siphon pipe P32. The pressure in the depressurizing container thus decreases. (In this case, the liquid discharging speed through the siphon pipe P32 is set at a value sufficiently greater than the liquid injection speed by the pump.) Since the pressure in the depressurizing container 11 decreases, the container 11 is a depressurizer.

Gas in the container 2 is sucked through the pipe P3 into the depressurizing container 11. Since the amount of liquid discharged from the container 11, i.e. the amount of gas sucked in is set to be large enough, liquid above the remaining liquid level L11 of the liquid E13 in the container 3 flows through the pipe P4 into the container 2 and mixes with liquid E12. Further, gas is blown into the mixture of liquids E12, E13 in the container 2, thus stirring the liquid mix (if the pipe P4 is open into the liquid mix).

Figure 5:
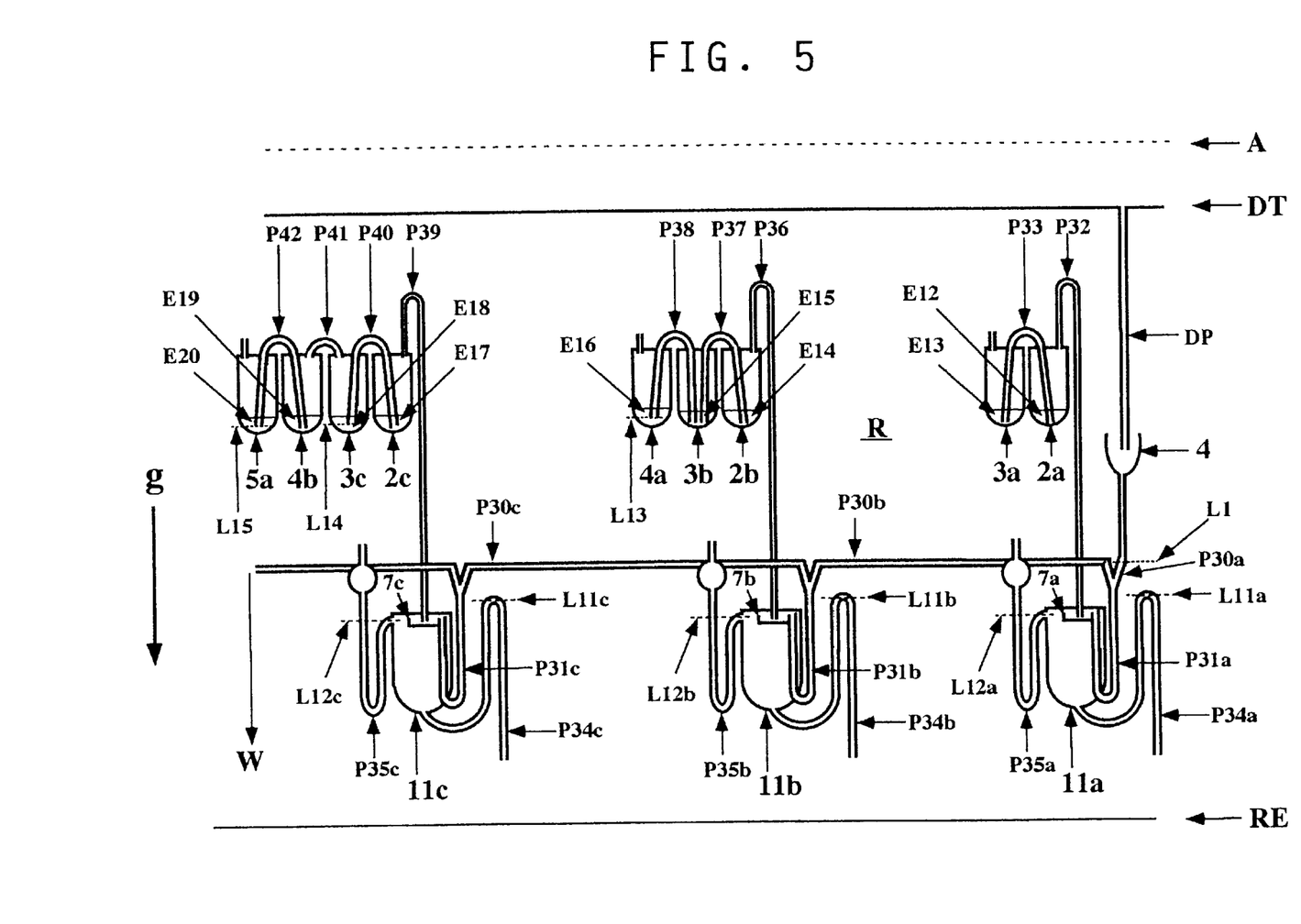
FIG. 5 is a view showing the third embodiment in which a depressurizing container is used.

FIG. 5 shows a third embodiment of the method according to the present invention of transferring a liquid specimen in a container on the rotor into another container on the rotor by means of a depressurizing container. It is a variation of the arrangement of FIG. 2B. It shows a depressurizing container 11a as a first depressurizer, a depressurizing container 11b as a second depressurizer, and a depressurizing container 11c as a third depressurizer that are arranged in series on the centrifugal rotor R, and containers (2a, 3a), (2b, 3b, 4a), (2c, 3c, 4b, 5a) subordinate to the respective first, second and third depressurizing containers 11a, 11b, 11c, respectively, and shows how they communicate on the circumference of the rotor.

When liquid injected into the rotating rotor R flows through one of the stages of the distributor DT, injection pipe DP, liquid reservoir 4, end pipe P30a, U-pipe P31a into a fluid reservoir tray 7a of the depressurizing container 11a, overflowing liquid increases the liquid level in the depressurizing container 11a, exhausting gas in the container 11a through the exhaust pipe P35a. When the liquid level further increases and exceeds the inlet level L12a of the exhaust pipe P35a, liquid now flows into the exhaust pipe P35a, closing air communication therethrough. When the liquid level further increases and exceeds the siphon-activating level L11a, liquid in the depressurizing container 11a is discharged through a siphon pipe P34a. The pressure in the container 11a thus decreases. (In this case, the liquid discharging speed through the siphon pipe P34a is set at a value sufficiently greater than the liquid injection speed by the pump.)

Gas in the container 2a is sucked through the pipe P32 into the depressurizing container 11a. Since the amount of liquid discharged from the container 11a, i.e. the amount of gas sucked in is set to be large enough, liquid E13 in the container 3a is entirely fed into the container 2a (because one end of the pipe P33 extends to the bottom of the container 3a), and mixes with liquid E12. Further, gas is blown into the mixture of liquids E12, E13 in the container 2a, thus stirring the liquid mix (if the pipe P33 is open into the liquid mix).

When the liquid in the depressurizing container 11a has been discharged, gas communication through the pipes P31a, P35a, P32 and P34a is closed (by the liquid that has flown into the pipes).

Thus, when liquid is continuously injected from the pump, the pressure in the depressurizing container 11a will turn positive, so that the flow of liquid into the container 11a is limited. When the level of injected liquid exceeds the level L1, it flows through the pipe P30b and U-pipe P31b into a liquid reservoir tray 7b in the depressurizing container 11b. The liquid increases the liquid level in the container 11b, thus exhausting gas in the container 11b through the exhaust pipe P35b. When the liquid level further increases and exceeds the inlet level L12b of the exhaust pipe P35b, liquid now flows into the exhaust pipe P35b, closing air communication therethrough. When the liquid level further increases and exceeds the siphon-activating level L11b, liquid in the depressurizing container 11b is discharged through a siphon pipe P34b. The pressure in the container 11b thus decreases. (The liquid discharging speed through the siphon pipe P34b is set at a value sufficiently greater than the liquid injection speed by the pump.)

Gas in the container 2b is sucked through the pipe P36 into the depressurizing container 11b. Since the amount of liquid discharged from the container 11b, i.e. the amount of gas sucked in is large enough, liquid E15 in the container 3b is entirely fed through the pipe P37 into the container 2b (because one end of the pipe P37 extends to the bottom of the container 3b). Also, liquid E16 in the container 4a at a level higher than the remaining liquid level L13 is discharged through the pipe P38, container 3b, pipe P37 into the container 2b. Liquids E14, E15, E16 are thus mixed together. Further, gas is blown into the mixture of liquids E14, E15, E16 in the container 2b, thus stirring the liquid mix (if the pipe P37 is open into the liquid mix).

When the liquid in the depressurizing container 11b has been discharged, gas communication through the pipes P31b, P35b, P36 and P34b is closed (by the liquid that has flown into the pipes).

Thus, when liquid is continuously injected from the pump in this state, the pressure in the depressurizing container 11b will turn positive, so that the flow of liquid into the container 11b is limited. When the level of injected liquid exceeds the level L1, it flows through the pipe P30c and U-pipe P31c into a liquid reservoir tray 7c in the depressurizing container 11c. The liquid increases the liquid level in the container 11c, thus exhausting gas in the container 11c through the exhaust pipe P35c. When the liquid level further increases and exceeds the inlet level L12c of the exhaust pipe P35c, liquid now flows into the exhaust pipe P35c, closing air communication therethrough. When the liquid level further increases and exceeds the siphon-activating level L11c, liquid in the container 11c is discharged through a siphon pipe P34c. The pressure in the container 11c thus decreases. (The liquid discharging speed through the siphon pipe P34c is set at a value sufficiently greater than the liquid injection speed by the pump.)

Gas in the container 2c is sucked through the pipe P39 into the depressurizing container 11c. Since the amount of liquid discharged from the container 11c, i.e. the amount of gas sucked in is large enough, liquid E18 in the container 3c at a level higher than the remaining liquid level is fed through the pipe P40 into the container 2c and mixes with liquid E17. Also, liquid E20 in the container 5a at a level higher than the remaining liquid level L15 is discharged through the pipe P42 into the container 4b, and mixes with liquid E19. Further, gas is blown into the mixture of liquids E17 and E18 in the container 2c, and the mixture of liquids E19 and E20 in the container 4b, thus stirring the liquid mixes (if the pipes P40 and P42 are open into the liquid mixes).

When the liquid in the depressurizing container 11c has been discharged, gas communication through the pipes P31c, P35c, P39 and P34c is closed (by the liquid that has flown into the pipes).

Thus, when liquid is continuously injected by the pump in this state, the pressure in the depressurizing container 11c will turn positive, so that the flow of liquid into the container 11c is limited. When the level of injected liquid exceeds the level L11, it overflows and is discharged into the liquid reservoir W.

In the arrangement of FIG. 5, three depressurizing containers 11a, 11b, 11c are arranged in series. But the number of depressurizing containers may be increased if necessary. The number of containers subordinate to each of the depressurizing containers 11a, 11b, 11c may also be increased if necessary. Further, the containers may be communicated in any other way.

Figure 6:
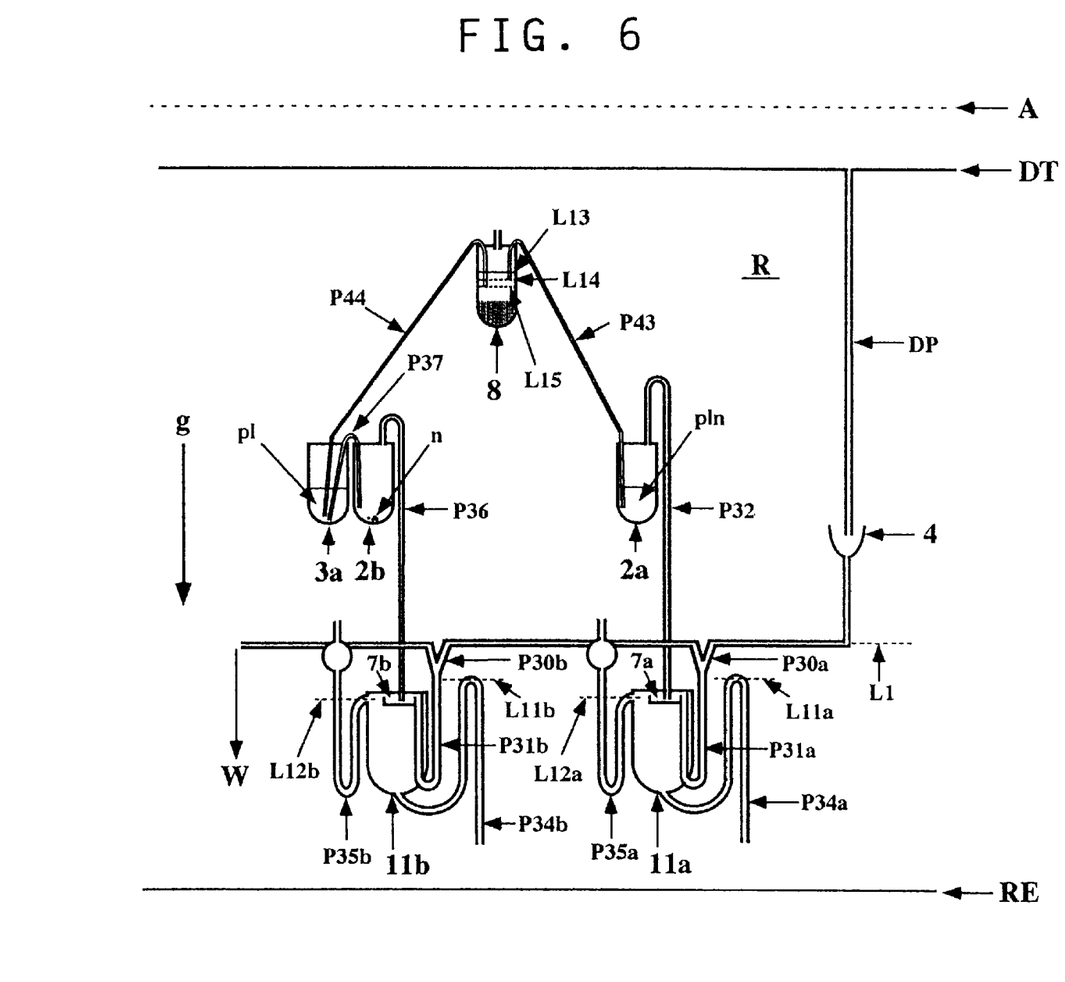
FIG. 6 is a view showing the fourth embodiment in which a depressurizing container is used.

FIG. 6 shows a fourth embodiment in which a depressurizing container is used. It is another variation of the arrangement of FIG. 2B. It shows a depressurizing container 11a as a first depressurizer, a depressurizing container 11b as a second depressurizer, containers 2a, 2b and 3b, and a plasma separating container 8, all arranged on the centrifugal rotor R. It shows how they communicate on the circumference of the rotor.

In the plasma separating container 8, 0.5 ml human blood (extracted from one of the inventors of the present invention) to which was added a trace amount of heparin was put. In the container 2a, 0.9 ml pyrophosphate buffer p1n (pH8.3, 0.1M) containing reduced nicotinamide adenine dinucleotide ($10^{-3}$M) and pyruvate ($10^{-3}$M) as a reaction reagent was put. In the container 2b, 0.66 mg of reduced nicotinamide adenine dinucleotide powder n was put. In the container 3a, 0.9 ml pyrophosphate buffer p1 (pH8.3, 0.1M) containing pyruvate ($10^{-3}$M) was put.

The rotating centrifugal rotor R was observed visually while illuminating it with a lamp blinking synchronously with the rotation of the rotor.

After the blood has been centrifuged by rotating the rotor at 2000 rpm (about three minutes), the rotor R was decelerated to 800 rpm, and liquid (water) was injected from a pump. Liquid was fed through one of the stages of the distributor DT, injection pipe DP, liquid reservoir 4, pipe P30a, U-pipe P31a into a liquid reservoir tray 7a of the depressurizing container 11a. Overflowing liquid increased the liquid level in the container 11a, thus exhausting gas in the container 11a through the exhaust pipe 35a. When the liquid level further increases and exceeds the inlet level L12a of the exhaust pipe P35a, liquid now flows into the exhaust pipe P35a, closing air communication therethrough. When the liquid level further increases and exceeds the siphon-activating level L11a, liquid in the container 11a is discharged through a siphon pipe P34a. The pressure in the container 11a thus decreases. (In this case, the liquid discharging speed through the siphon pipe P34a is set at a value sufficiently greater than the liquid injection speed from the pump.)

Gas in the container 2a was sucked through the pipe P32 into the container 11a. Since the amount of liquid discharged from the container 11a, i.e. the amount of gas sucked in was large enough, plasma in the container 8 at the level between levels L13 and L14 was fed through the pipe P43 into the container 2a and mixed with the liquid p1n in the container 2a. Further, gas was blown into the liquid mix in the container 2a to agitate it (because the pipe P43 is open into the liquid).

When the liquid in the depressurizing container 11a has been discharged, gas communication through the pipes P31a, P35a, P32 and P34a is closed (by the liquid that has flown into the pipes).

Thus, when liquid is continuously injected by the pump in this state, the pressure in the container 11a will turn positive, so that the flow of liquid into the container 11a is limited. When the level of injected liquid exceeds the level L1, it is discharged through the pipe P30b, U-pipe P31b into the liquid reservoir tray 7b of the depressurizing container 11b. Overflowing liquid increases the liquid level in the container 11b, thus exhausting gas in the container 11b through the exhaust pipe P35b. When the liquid level further increases and exceeds the inlet level L12b of the exhaust pipe P35b, liquid now flows into the exhaust pipe P35b, closing air communication therethrough. When the liquid level further increases and exceeds the siphon-activating level L11b, liquid in the depressurizing container 11b is discharged through a siphon pipe P34b. The pressure in the container 11b thus decreases. (The liquid discharging speed through the siphon pipe P34b is set at a value sufficiently greater than the liquid injection speed from the pump.)

Gas in the container 2b was sucked through the pipe P36 into the depressurizing container 11b. Since the amount of liquid discharged from the container 11b, i.e. the amount of gas sucked in was large enough, plasma in the container 8 at the level between levels L14 and L15 was fed through the pipe P44 into the container 3a and mixed with the liquid [0.9 ml pyrophosphate buffer p1 containing pyruvate] in the container 3a, then fed through pipe P37 into the container 2b, thus dissolving reduced nicotinamide adenine dinucleotide powder n. Further, gas was blown into the liquid mix in the container 2b to agitate it (because the pipe P37 is open into the liquid).

When the liquid in the container 11b has been discharged, gas communication through the pipes P31b, P35b, P36 and P34b is closed (by the liquid that has flown into the pipes).

Thus, when liquid is continuously injected from the pump in this state, the pressure in the container 11b will turn positive, so that the flow of liquid into the container 11b is limited. When the level of injected liquid exceeds the level L1, it overflows and is discharged into the liquid reservoir W.

How liquid moved and mixed and how gas was blown into liquid was visually observed using a device that permits visual observation under synchronously blinking illumination as described above, and the results of observation were duly recorded.

The supernatant of liquid in the plasma separating container 8 was fed 0.1 ml each into the container 2a and through the container 3a into the container 2b and mixed with reaction reagents. By the action of lactate dehydrogenase contained in blood (plasma), reduced nicotinamide adenine dinucleotide in the pyrophosphate buffer was oxidized. By measuring the oxidizing speed in terms of absorbance of light of 340 nm in wavelength with a phonometer provided outside the rotor, it was possible to automatically determine the lactate dehydrogenase activity in the blood (plasma).

FIG. 7 shows a fifth embodiment of the method according to the present invention of transferring a liquid specimen in one container on the rotor into another container on the rotor by means of a small depressurizing container. It shows a small depressurizing container 21 as a depressurizer, a container 2 containing liquid E12 and a container 3 containing liquid E13, all arranged on the centrifugal rotor R, and shows how they communicate with each other.

When a liquid is injected into the distributor DT on the rotating rotor R, the liquid flows through the injection pipe DP, liquid reservoir 4, end pipe P1, U-pipe P30 into a small depressurizing container 21, and soon quickly discharged through the discharge pipe P32 by centrifugal force. The pressure in the small depressuring container 21 thus drops. Since the pressure in the container 21 decreases, it functions as a depressurizer.

Gas in the container 2 is sucked through the pipe P3 into the small depressurizing container 21. Since the amount of gas discharged from the container 21 is large enough, liquid at a level higher than the remaining liquid level L11 of the liquid E13 in the container 3 flows through the pipe P4 into the container 2 and mixes with liquid E12. Further, gas is blown into the mixture of liquids E12, E13 in the container 2, thus stirring the liquid mix (if the pipe P4 is open into the liquid mix).

Figure 8:
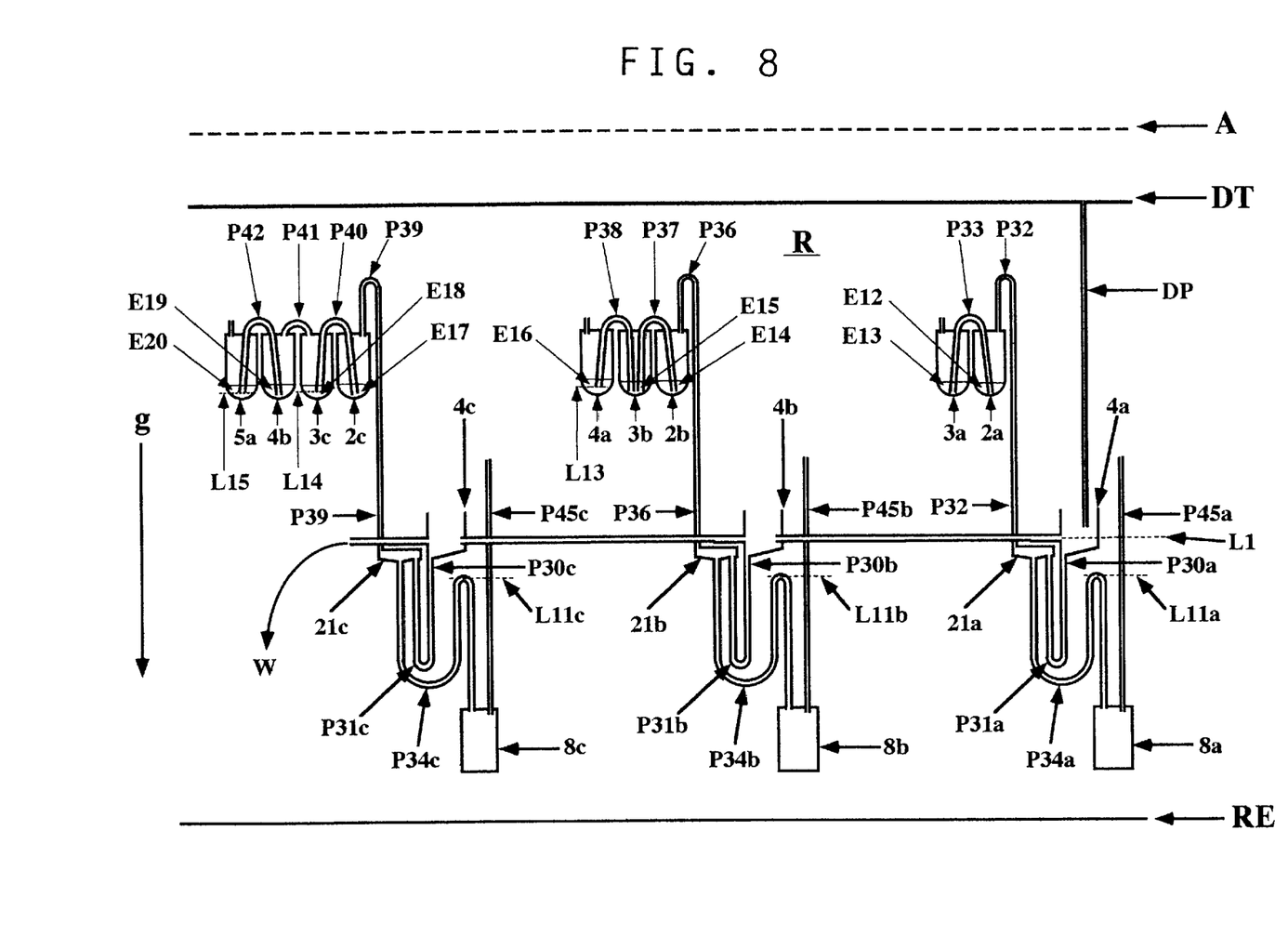
FIG. 8 is a view showing the sixth embodiment in which a small depressurizing container is used.

FIG. 8 shows a sixth embodiment of the method according to the present invention of transferring a liquid specimen in a container on the rotor into another container on the rotor by means of a small depressurizing container. It shows a small depressurizing container 21a as a first depressurizer, a small depressurizing container 21b as a second depressurizer, and a small depressurizing container 21c as a third depressurizer that are arranged in series on the centrifugal rotor R, and containers (2a, 3a), (2b, 3b, 4a), (2c, 3c, 4b, 5a) subordinate to the respective containers 21a, 21b, 21c. It shows how they communicate on the circumference of the rotor.

When liquid injected into the rotating rotor R flows through one of the stages of the distributor DT, injection pipe DP, liquid reservoir 4a, end pipe P30a, U-pipe P31a into the small depressurizing container 21a, it is instantly and quickly discharged through the discharge pipe P34a into a fluid reservoir 8a (gas in the reservoir 8a is discharged through the pipe P45a), so that the pressure in the small depressurizing container 21a decreases.

Gas in the container 2a is sucked through the pipe P32 into the small depressurizing container 21a. Since the amount of gas sucked into the container 21a and discharged through the discharge pipe P34a is large enough, liquid E13 in the container 3a is entirely fed through the pipe P33 into the container 2a (because one end of the pipe P33 extends to the bottom of the container 3a), and mixes with liquid E12. Further, gas is blown into the mixture of liquids E12, E13 in the container 2a, thus stirring the liquid mix (if the pipe P33 is open into the liquid mix).

When liquid is continuously injected by the pump in this state, the fluid reservoir 8a is filled up with liquid, and the liquid enters the pipe P45a. When the liquid level in the pipe reaches L1, the pressure in the small depressurizing container 21a turns positive, so that the flow of liquid into the container 21a is limited. Overflowing liquid flows through the fluid reservoir 4b, end pipe P30b, U-pipe P31b into the small depressurizing container 21b, and is instantly and quickly discharged through the discharge pipe P34b into the fluid reservoir 8b (gas in the reservoir 8b is discharged through the pipe P45b), so that the pressure in the small depressurizing container 21b decreases.

Gas in the container 2b is sucked through the pipe P36 into the container 21b. Since the amount of gas sucked into the small depressurizing container 21b and discharged through the discharge pipe P34b is large enough, liquid E15 in the container 3b is entirely fed through the pipe P37 into the container 2b (because one end of the pipe P37 extends to the bottom of the container 3b). Also, liquid E16 in the container 4a at a level higher than the remaining liquid level L13 is fed through the pipe 38 into the container 3b and through the pipe P37 into the container 2b. Liquids E14, E15, E16 are thus mixed together in the container 2b. Further, gas is blown into the mixture of liquids E14, E15 and E16, thus stirring the liquid mix (if the pipe P37 is open into the liquid mix).

When liquid is continuously injected by the pump in this state, the fluid reservoir 8b is filled up with liquid, and the liquid enters the pipe P45b. When the liquid level reaches L1, the pressure in the small depressurizing container 21b turns positive, so that the flow of liquid into the container 21b is limited. Overflowing liquid flows through the fluid reservoir 4c, end pipe P30c, U-pipe P31c into the small depressurizing container 21c, and is instantly and quickly discharged through the discharge pipe P34c into the fluid reservoir 8c (gas in the reservoir 8c is discharged through the pipe P45c), so that the pressure in the container 21c decreases.

Gas in the container 2c is sucked through the pipe P39 into the small depressurizing container 21c. Since the amount of gas sucked into the container 21c and discharged through the discharge pipe P34c is large enough, liquid E18 in the container 3c above the remaining liquid level L14 is fed through the pipe P40 into the container 2c and mixes with liquid E17. Liquid E20 in the container 5a above the remaining liquid level L15 is fed through the pipe P42 into the container 4b and mixes with liquid E19. Further, gas is blown into the mixture of liquids E17 and E18 in the container 2c and the mixture of liquids E19 and E20 in the container 4b, thus stirring the liquid mixes (if the pipes P40, P42 are open into the liquid mixes).

When liquid is continuously injected by the pump in this state, the fluid reservoir 8c is filled up with liquid, and the liquid enters the pipe P45c. When the liquid level reaches L1, the pressure in the small depressurizing container 21c turns positive, so that the flow of liquid into the container 21c is limited. Overflowing liquid is discharged into the reservoir W.

In the arrangement of FIG. 8, three depressurizing containers 21a, 21b, 21c are arranged in series. But the number of depressurizing containers may be increased if necessary. The number of containers subordinate to each of the depressurizing containers 21a, 21b, 21c may also be increased if necessary. Further, the containers may be communicated in any other way.

While main embodiments of the present invention have been described, the present invention is not limited to these specific embodiments. These embodiments are susceptible to various modifications within the scope of the invention.

According to the present method, it is possible to not manually but automatically transfer a liquid specimen in one container placed on a centrifugal rotor into another container on the same rotor in a safe and reliable manner without stopping the rotor while preventing bacterial contamination. This permits separation, purification, analysis, etc. of a liquid specimen. The present method is thus usable in medical, pharmacological, biological and many other fields. The following are only some of the many advantages of the present invention.

1) It is possible to automatically separate and purify cultured cells while preventing contamination by microorganisms.
2) It is possible to automatically separate or fraction blood components while preventing contamination by microorganisms.
3) It is possible to automatically separate and purify e.g. DNA's using an organic solvent while preventing contamination by microorganisms.
4) It is possible to achieve an intended object by adapting the combination of various conditions such as ① size, arrangement and positioning of containers (pressurizers, depressurizers and subordinate containers for specimen and reagent), ② liquid injection speed and timing, ③ rotating speed of centrifugal rotor, and setting an automatic program for working steps (centrifuging of specimens, discharge of supernatants, feeding of reagents, and repetition thereof, etc.).

What is claimed is:

1. A method of transferring a liquid specimen in one container on a centrifugal rotor into another container on the same rotor, the method comprising injecting a liquid into a pressurizing container communicating with said one container while said rotor is rotating, to increase the volumetric ratio of liquid in said pressurizing container, thereby increasing the gas pressure in said pressurizing container and thus the gas pressure in said one container, thereby transferring said liquid specimen in said one container under pressure into said another container.

2. A method of transferring a liquid specimen in one container on a centrifugal rotor into another container on the same rotor, the method comprising injecting a liquid into a depressurizing container communicating with said another container while said rotor is rotating, thereby discharging the liquid from said depressurizing container by centrifugal force to decrease the volumetric ratio of liquid in said depressurizing container to reduce the gas pressure in said depressurizing container and thus the gas pressure in said another container, and thereby sucking said liquid specimen in said one container into said another container.

3. A method of transferring a liquid specimen in one container on a centrifugal rotor into another container on the same rotor, the method comprising injecting a liquid into a small depressurizing container communicating with said another container while said rotor is rotating, discharging the liquid quickly from said small depressurizing container through a discharge tube by centrifugal force to reduce the gas pressure in said small depressurizing container and thus the gas pressure in said another container, and thereby sucking said liquid specimen in said one container into said another container.

* * * * *